(12) United States Patent
Cawley et al.

(10) Patent No.: US 8,721,693 B2
(45) Date of Patent: May 13, 2014

(54) CERVICAL PLATE LOCKING MECHANISM AND ASSOCIATED SURGICAL METHOD

(75) Inventors: Trace Cawley, Boca Raton, FL (US); David Crook, Mineola, TX (US)

(73) Assignee: US Spine, Inc., Salt Lake City, UT (US)

( * ) Notice: Subject to any disclaimer, the term of this patent is extended or adjusted under 35 U.S.C. 154(b) by 1218 days.

(21) Appl. No.: 11/875,072

(22) Filed: Oct. 19, 2007

(65) Prior Publication Data
US 2008/0288001 A1  Nov. 20, 2008

Related U.S. Application Data

(63) Continuation-in-part of application No. 11/804,545, filed on May 18, 2007.

(51) Int. Cl.
*A61B 17/80* (2006.01)
*A61B 17/84* (2006.01)

(52) U.S. Cl.
USPC .......................... 606/289; 606/290

(58) Field of Classification Search
USPC .............. 606/280, 288, 289, 290, 291, 327
See application file for complete search history.

(56) References Cited

U.S. PATENT DOCUMENTS

| | | | |
|---|---|---|---|
| 3,741,205 A | 6/1973 | Markolf et al. | |
| 4,175,555 A | 11/1979 | Herbert | |
| 5,120,171 A | 6/1992 | Lasner | |
| 5,226,766 A | 7/1993 | Lasner | |
| 5,360,452 A | 11/1994 | Engelhardt et al. | |
| 5,417,533 A | 5/1995 | Lasner | |
| 5,492,442 A | 2/1996 | Lasner | |
| 5,562,672 A | 10/1996 | Huebner et al. | |
| 5,601,553 A | 2/1997 | Trebing et al. | |
| 5,643,269 A | 7/1997 | Harle | |
| 5,681,311 A * | 10/1997 | Foley et al. | 606/283 |
| 5,871,486 A | 2/1999 | Huebner et al. | |
| 5,899,906 A | 5/1999 | Schenk | |
| 5,947,965 A | 9/1999 | Bryan | |
| 5,964,768 A | 10/1999 | Huebner | |
| 5,997,541 A | 12/1999 | Schenk | |
| 6,048,344 A | 4/2000 | Schenk | |
| 6,129,730 A | 10/2000 | Bono et al. | |
| 6,224,602 B1 | 5/2001 | Hayes | |
| 6,293,949 B1 | 9/2001 | Justis et al. | |
| 6,331,179 B1 * | 12/2001 | Freid et al. | 606/279 |
| 6,375,657 B1 | 4/2002 | Doubler et al. | |
| 6,692,503 B2 | 2/2004 | Foley et al. | |
| 6,695,846 B2 * | 2/2004 | Richelsoph et al. | 606/71 |
| 6,730,091 B1 | 5/2004 | Pfefferle et al. | |
| 6,761,719 B2 | 7/2004 | Justis et al. | |
| 7,001,389 B1 | 2/2006 | Navarro et al. | |

(Continued)

*Primary Examiner* — Christian Sevilla
(74) *Attorney, Agent, or Firm* — Phillips Ryther & Winchester; Matthew D. Thayne

(57) ABSTRACT

The cervical plate locking mechanism of the present invention is elegant in its design and effective in its performance, and utilizes a plate with holes that each incorporate a locking lip structure and locking screws that each incorporate a head portion having petal structures that are outwardly biased prior to insertion via an internally-disposed c-ring or the like. Advantageously, the lead-in torque of each of the locking screws is less than the lead-out torque of each of the locking screws. Thus, reverse threading or backing out is prevented. Alternatively, the cervical plate locking mechanism of the present invention utilizes a locking plate having petal structures that are inwardly biased prior to insertion of the head portion of the locking screws via an externally-disposed c-ring or the like.

11 Claims, 12 Drawing Sheets

(56) References Cited

U.S. PATENT DOCUMENTS

| | | |
|---|---|---|
| 7,322,983 B2 | 1/2008 | Harris |
| 2002/0016595 A1 | 2/2002 | Michelson |
| 2002/0120273 A1 | 8/2002 | Needham et al. |
| 2003/0105462 A1* | 6/2003 | Haider ............... 606/69 |
| 2004/0104047 A1* | 6/2004 | Peter ............... 175/40 |
| 2004/0220571 A1 | 11/2004 | Assaker et al. |
| 2004/0236333 A1 | 11/2004 | Lin |
| 2005/0096657 A1* | 5/2005 | Autericque et al. ........... 606/69 |
| 2005/0149027 A1* | 7/2005 | Campbell et al. ............. 606/70 |
| 2006/0122604 A1* | 6/2006 | Gorhan et al. ............... 606/69 |
| 2006/0149263 A1 | 7/2006 | Newcomb et al. |
| 2007/0123884 A1* | 5/2007 | Abdou ............... 606/69 |
| 2007/0203492 A1 | 8/2007 | Needham et al. |

* cited by examiner

CERVICAL PLATE LOCKING MECHANISM AND ASSOCIATED SURGICAL METHOD

CROSS-REFERENCE TO RELATED APPLICATION(S)

The present patent application is a continuation-in-part of co-pending U.S. patent application Ser. No. 11/804,545 to Cawley, filed on May 18, 2007, and entitled "CERVICAL PLATE LOCKING MECHANISM AND ASSOCIATED SURGICAL METHOD," the contents of which are incorporated in full by reference herein.

FIELD OF THE INVENTION

The present invention relates generally to a cervical plate locking mechanism and an associated surgical method. More specifically, the present invention relates to a cervical plate locking mechanism that includes one or more novel locking screws and a novel plate that works cooperatively therewith. The cervical plate locking mechanism, the one or more novel locking screws, and the novel plate are used for the fixation/stabilization of the cervical spine; alternatively, the fixation/stabilization of the lumbar spine; alternatively, the fixation/stabilization of the sacral spine; the placement of bone grafts, biocompatible inserts, or the like; alternatively, the fixation/stabilization of other anatomical structures; and, alternatively, the fixation/stabilization of other non-anatomical structures.

BACKGROUND OF THE INVENTION

The vertebrae of the human spine are generally arranged in a column, with an intervertebral disc disposed between each. These intervertebral discs transmit forces and perform a "cushioning" function. As a result of the stresses and strains continuously applied to the intervertebral discs, as well as disease, degeneration and/or deformity is relatively common. Typically, diseased, degenerated, and/or deformed intervertebral discs are treated by removal and the insertion of an implant, anatomical (i.e. a bone graft) or mechanical (i.e. a biocompatible insert), in the associated intervertebral space. The adjacent vertebrae are preferably immobilized using a plate, such as a cervical plate, during bone graft or biocompatible insert placement and subsequently until they fuse, for example.

Conventional cervical plates typically include a plurality of screw holes and one or more access holes, through which one or more bone grafts or other biocompatible inserts are placed. These cervical plates may span one or multiple levels, with a level defined by the presence of an intervertebral space, and are secured to the vertebrae of the spine using a plurality of bone screws. Absent some sort of locking mechanism, these bone screws tend to reverse thread, or back out, over time. This reverse threading or backing out is obviously problematic. Various locking mechanisms exist in the art for preventing reverse threading or backing out, and typically involve the use of polymeric bushings, securing caps, securing cover plates, novel thread designs, and the like that prevent the bone screws from disengaging the vertebrae and/or cervical plate subsequent to installation. Many of these locking mechanisms are ineffective, overly complicated, cumbersome to implement, and/or unnecessarily expensive. Thus, what is still needed in the art is a robust, simple, and inexpensive cervical plate locking mechanism.

BRIEF SUMMARY OF THE INVENTION

In various exemplary embodiments, the present invention provides such a robust, simple, and inexpensive cervical plate locking mechanism. The cervical plate locking mechanism of the present invention is elegant in its design and effective in its performance, and utilizes a plate with holes that each incorporate a locking lip structure, or receiving well, and locking screws that each incorporate a head portion having petal structures that are outwardly biased prior to insertion via an internally-disposed c-ring or the like. Advantageously, the lead-in torque of each of the locking screws is less than the lead-out torque of each of the locking screws. Thus, reverse threading or backing out is prevented.

In one exemplary embodiment, the present invention provides a cervical plate locking mechanism, including: a plate defining one or more holes configured to receive one or more locking screws, wherein the plate includes an outer surface, an interior portion, and an inner surface, each of the one or more holes having an inside diameter that is smaller adjacent to the outer surface than at the interior portion, thereby forming a lip structure associated with each of the one or more holes adjacent to the outer surface; and one or more locking screws, each including: a threaded portion configured to pass through one of the one or more holes of the plate and securely engage an anatomical structure; and a head portion attached to the threaded portion configured to securely engage the lip structure associated with one of the one or more holes of the plate. Preferably, the interior of the plate at each of the one or more holes is curved such that a lead-in torque of each of the one or more locking screws is less than a lead-out torque of each of the one or more locking screws. The head portion of each of the one or more locking screws includes a plurality of petal structures disposed about a central driver bore, each of the plurality of petal structures including an inner groove disposed adjacent to the central driver bore. Optionally, the plurality of petal structures disposed about the central driver bore are outwardly biased. Each of the one or more locking screws also includes a c-ring selectively disposed within the inner groove disposed adjacent to the central driver bore, the c-ring configured to outwardly bias the plurality of petal structures disposed about the central driver bore. Each of the one or more holes defined by the plate is configured to receive one of the one or more locking screws one of perpendicularly and at an angle.

In another exemplary embodiment, the present invention provides a method for using a cervical plate locking mechanism, including: providing a plate defining one or more holes configured to receive one or more locking screws, wherein the plate includes an outer surface, an interior portion, and an inner surface, each of the one or more holes having an inside diameter that is smaller adjacent to the outer surface than at the interior portion, thereby forming a lip structure associated with each of the one or more holes adjacent to the outer surface; and providing one or more locking screws, each including: a threaded portion configured to pass through one of the one or more holes of the plate and securely engage an anatomical structure; and a head portion attached to the threaded portion configured to securely engage the lip structure associated with one of the one or more holes of the plate. Preferably, the interior of the plate at each of the one or more holes is curved such that a lead-in torque of each of the one or more locking screws is less than a lead-out torque of each of the one or more locking screws. The head portion of each of the one or more locking screws includes a plurality of petal structures disposed about a central driver bore, each of the plurality of petal structures including an inner groove disposed adjacent to the central driver bore. Optionally, the plurality of petal structures disposed about the central driver bore are outwardly biased. Each of the one or more locking screws also includes a c-ring selectively disposed within the inner groove disposed adjacent to the central driver bore, the c-ring configured to outwardly bias the plurality of petal structures disposed about the central driver bore. Each of the one or more holes defined by the plate is configured to receive one of the one or more locking screws one of perpendicularly and at an angle.

In a further exemplary embodiment, the present invention provides a cervical plate locking mechanism, including: a plate defining one or more holes configured to receive one or more locking screws, wherein the plate includes an outer surface, an interior portion, and an inner surface, each of the one or more holes having an inside diameter that is smaller adjacent to the outer surface than at the interior portion, thereby forming a lip structure associated with each of the one or more holes adjacent to the outer surface; and one or more locking screws, each including: a threaded portion configured to pass through one of the one or more holes of the plate and securely engage an anatomical structure; a head portion attached to the threaded portion configured to securely engage the lip structure associated with one of the one or more holes of the plate, wherein the head portion of each of the one or more locking screws includes a plurality of petal structures disposed about a central driver bore, each of the plurality of petal structures including an inner groove disposed adjacent to the central driver bore, wherein the plurality of petal structures disposed about the central driver bore are outwardly biased; and a c-ring selectively disposed within the inner groove disposed adjacent to the central driver bore, the c-ring configured to outwardly bias the plurality of petal structures disposed about the central driver bore. Preferably, the interior of the plate at each of the one or more holes is curved such that a lead-in torque of each of the one or more locking screws is less than a lead-out torque of each of the one or more locking screws. Each of the one or more holes defined by the plate is configured to receive one of the one or more locking screws one of perpendicularly and at an angle.

In a still further exemplary embodiment, the present invention provides a cervical plate locking mechanism, including: one or more locking screws, each including: a threaded portion configured to pass through one of one or more holes of a plate and securely engage an anatomical structure; a head portion attached to the threaded portion configured to securely engage a structure associated with one of the one or more holes of the plate, wherein the head portion of each of the one or more locking screws includes a plurality of petal structures disposed about a central driver bore, each of the plurality of petal structures including an inner groove disposed adjacent to the central driver bore, wherein the plurality of petal structures disposed about the central driver bore are outwardly biased; and a c-ring selectively disposed within the inner groove disposed adjacent to the central driver bore, the c-ring configured to outwardly bias the plurality of petal structures disposed about the central driver bore.

In a still further exemplary embodiment, the present invention provides a cervical plate locking mechanism, including: a locking plate defining one or more screw-receiving holes, wherein the perimeter of each of the one or more screw-receiving holes is substantially surrounded by one or more inwardly-biased petal structures; and one or more screws, wherein each of the one or more screws includes a head portion configured to selectively engage and be retained by the one or more inwardly-biased petal structures. The cervical plate locking mechanism also includes a biasing member disposed about the one or more inwardly-biased petal structures, wherein the biasing member is responsible for the inward bias of the one or more inwardly-biased petal structures. Optionally, the biasing member disposed about the one or more inwardly-biased petal structures includes a c-ring disposed about the one or more inwardly-biased petal structures. Preferably, the biasing member is disposed flush with or beneath a surface of the locking plate.

BRIEF DESCRIPTION OF THE DRAWINGS

The present invention is illustrated and described herein with reference to the various drawings, in which like reference numbers are used to denote like system components and/or method steps, as appropriate, and in which:

FIG. 2 is an exploded perspective view of one exemplary embodiment of the novel locking screw design of FIG. 1, the locking screw including a head portion that incorporates a plurality of petal structures that are outwardly biased by an internally-disposed c-ring or the like;

DETAILED DESCRIPTION OF THE INVENTION

As described above, in various exemplary embodiments, the present invention provides a robust, simple, and inexpensive cervical plate locking mechanism. The cervical plate locking mechanism of the present invention is elegant in its design and effective in its performance, and utilizes a plate with holes that each incorporate a locking lip structure, or receiving well, and locking screws that each incorporate a head portion having petal structures that are outwardly biased prior to insertion via an internally-disposed c-ring or the like. Advantageously, the lead-in torque of each of the locking screws is less than the lead-out torque of each of the locking screws. Thus, reverse threading or backing out is prevented.

Figure 1:
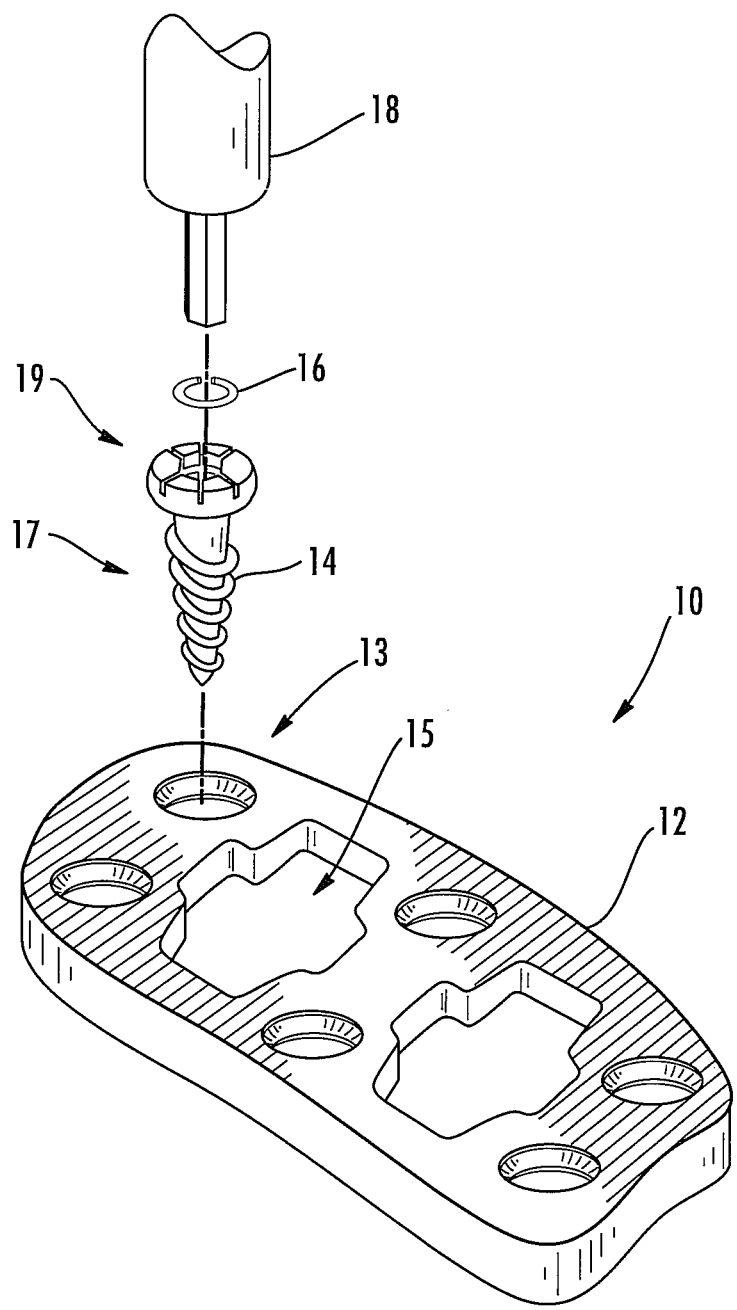
FIG. 1 is an exploded perspective view of one exemplary embodiment of the cervical plate locking mechanism of the present invention (being installed using a keyed screwdriver or the like), the cervical plate locking mechanism including both novel plate and novel locking screw designs.

FIG. 1 is an exploded perspective view of one exemplary embodiment of the cervical plate locking mechanism 10 of the present invention (being installed using a keyed screwdriver 18 or the like), the cervical plate locking mechanism 10 including both novel plate and novel locking screw designs, as are described in greater detail herein below. Specifically, the cervical plate locking mechanism 10 includes a plate 12 that is configured to be securely fixed to adjacent vertebrae of the cervical spine or the like via one or more locking screws 14 and one or more c-rings 16. The keyed screwdriver 18 is used to drive the one or more locking screws 14 through the plate 12 and into the adjacent vertebrae. The plate 12 includes one or more screw-receiving holes 13 and, optionally, one or more access holes 15 for the placement of one or more bone grafts, biocompatible inserts, or the like. Preferably, the plate 12 is manufactured from a biocompatible material and is sized such that it achieves its intended purpose. Material, shape, and size selection is well known to those of ordinary skill in the art. Each of the one or more locking screws 14 includes a threaded portion 17 and a head portion 19. The threaded portion 17 of each of the one or more locking screws 14 is configured to pass through the one or more screw-receiving holes 13 of the plate 12 and securely fix the plate 12 to the adjacent vertebrae. Thread selection is well known to those of ordinary skill in the art. The head portion 19 of each of the one or more locking screws 14 is configured to securely engage each of the one or more locking screws 14 with the plate 12. As described in greater detail herein below, the head portion 19 of each of the one or more locking screws 14 is outwardly biased by the c-ring 16, or by another comparable mechanism, which is selectively compressed, inserted into the head portion 19 of a given locking screw 14, and then allowed to expand. The c-ring 16, or other comparable mechanism, and the head portion 19 of the given locking screw 14 are again compressed and subsequently allowed to expand as they are inserted into a given screw-receiving hole 13 of the plate 12. Specifically, the head portion 19 of the given locking screw 14 is allowed to expand in the receiving well of the given screw-receiving hole 13. This insertion is accomplished using a matching flat, triangle, square, star, hexagon, octagon, or other keyed screwdriver 18, as appropriate. Preferably, the shape of the outside of the head portion 19 of each of the locking screws 14 substantially corresponds to the shape of the inside of the associated receiving well, although this is not a requirement.

Figure 2:
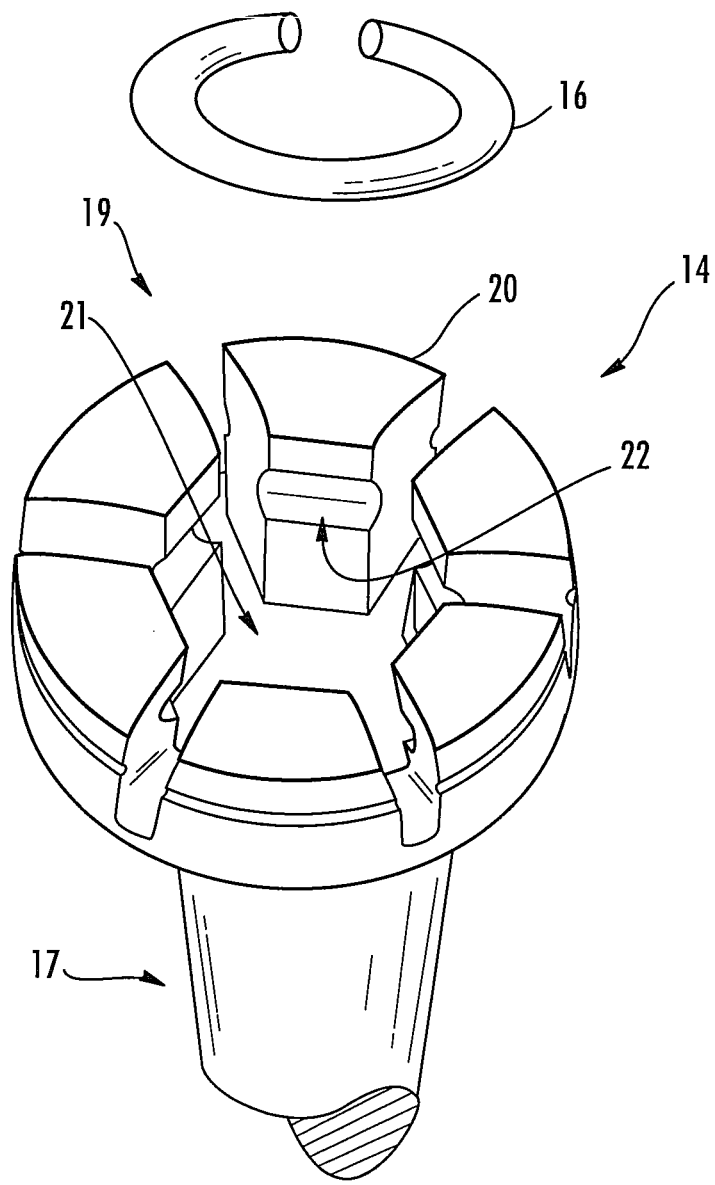
Figure 3:
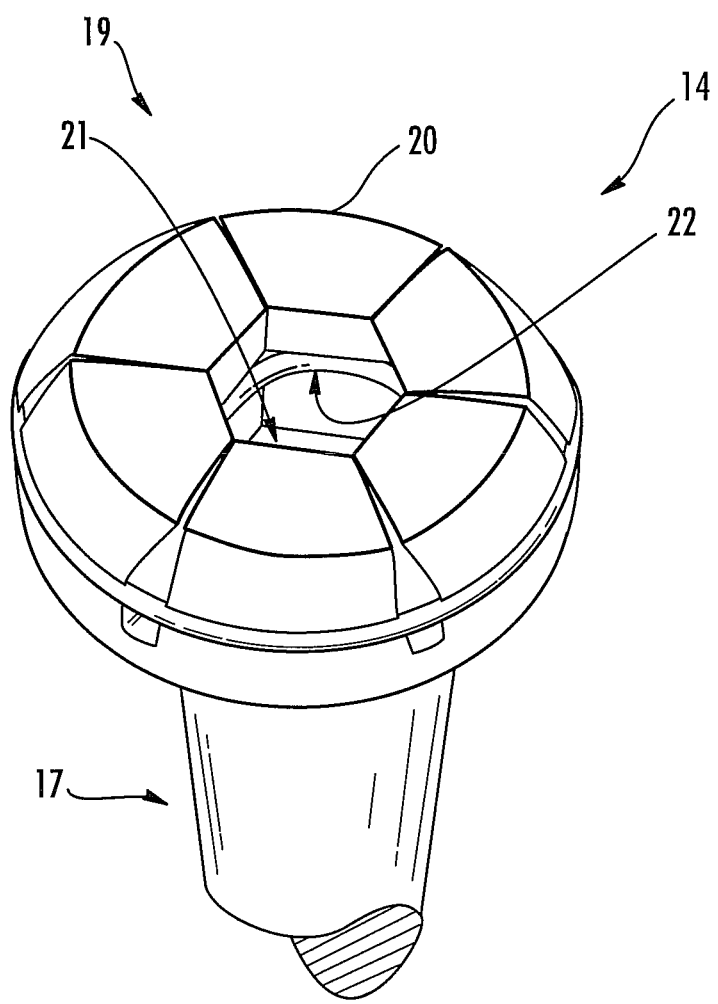
FIG. 3 is a perspective view of the novel locking screw design of FIGS. 1 and 2, the locking screw being in its "as inserted" state, with the c-ring being installed and the head portion being compressed.

FIG. 2 is an exploded perspective view of one exemplary embodiment of the novel locking screw design of FIG. 1, the locking screw 14 including a head portion 19 that incorporates a plurality of petal structures 20 that are outwardly biased by the internally-disposed c-ring 16 or the like. As described above, the c-ring 16, or other comparable mechanism, is selectively compressed, inserted into the head portion 19 of a given locking screw 14, and then allowed to expand. The c-ring 16, or other comparable mechanism, and the head portion 19 of the given locking screw 14 are again compressed and subsequently allowed to expand as they are inserted into a given screw-receiving hole 13 (FIG. 1) of the plate 12 (FIG. 1). Specifically, the head portion 19 of the given locking screw 14 is allowed to expand in the receiving well of the given screw-receiving hole 13. This insertion is accomplished using a matching flat, triangle, square, star, hexagon, octagon, or other keyed screwdriver 18 (FIG. 1), as appropriate. Preferably, the shape of the outside of the head portion 19 of each of the locking screws 14 substantially corresponds to the shape of the inside of the associated receiving well, although this is not a requirement. Accordingly, the head portion 19 of each of the locking screws 14 includes a plurality of concentrically-arranged petal structures 20 that are disposed around a central driver bore 21 that has a shape corresponding to that of the keyed screwdriver 18. In one exemplary embodiment, the plurality of petal structures 20 are formed by cutting concentrically-arranged slots into the head portion 19 of the locking screw 14. Thus, the plurality of petal structures 20 are integrally formed with the head portion 19 of the locking screw 14. Alternatively, the plurality of petal structures 20 are formed separately and then joined to the head portion 19 of the locking screw 14. The material characteristics or configuration of the plurality of petal structures 20 may impart the plurality of petal structures 20 with an inherent outward bias, independent of the c-ring 16 or other comparable mechanism, although this is not required. Preferably, the plurality of petal structures 20 define an inner groove 22 that is configured to receive and retain the c-ring 16 or other comparable mechanism within the head portion 19 of the locking screw 14. FIG. 2 illustrates the head portion 19 of the locking screw 14 in an "unlocked" configuration, with the plurality of petal structures 20 being "open," either due to the eventual insertion of the c-ring 16 or other comparable mechanism, or inherently. FIG. 3 illustrates the head portion 19 of the locking screw 14 in a "locked" configuration, with the plurality of petal structures 20 being "closed," either inherently or due to the eventual insertion of the head portion 19 of the locking screw 14 into a receiving well.

Figure 4:
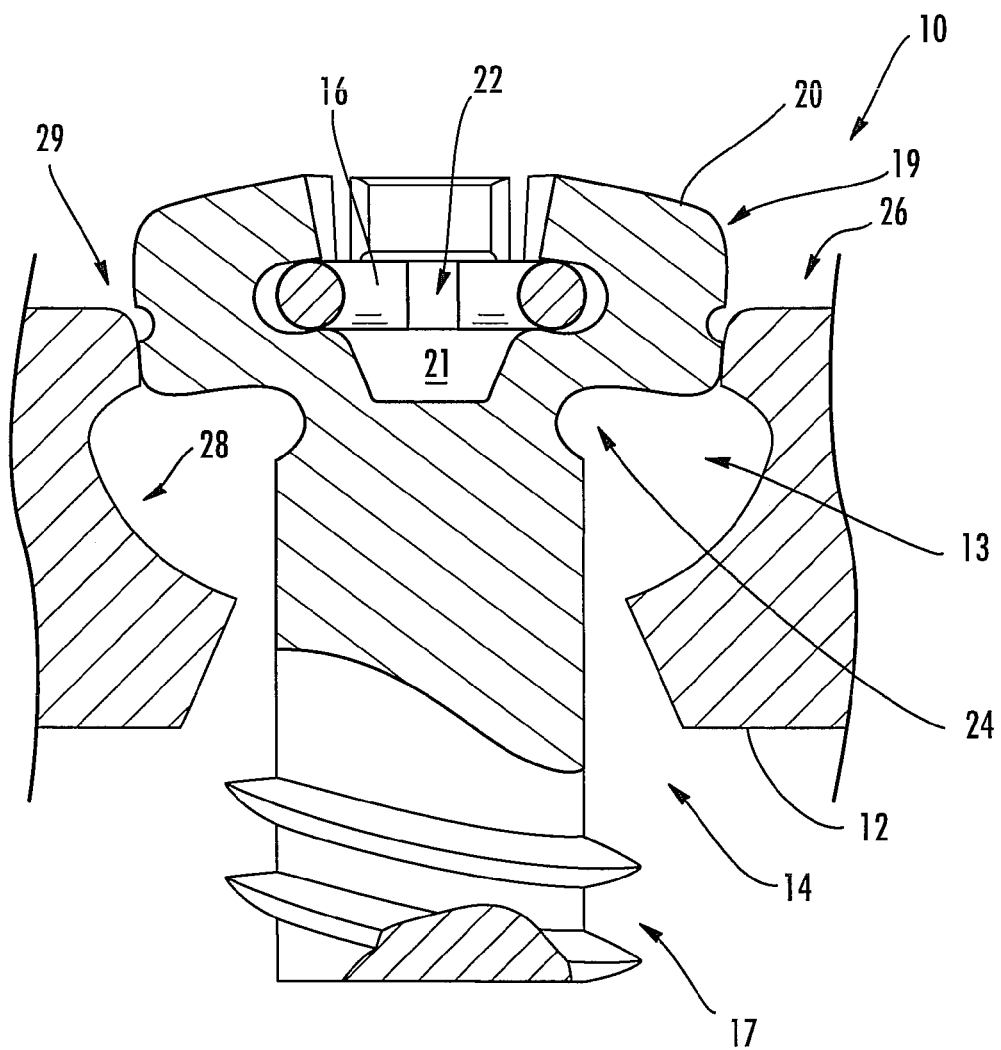
FIG. 4 is a partial cross-sectional view of the cervical plate locking mechanism of FIG. 1, the novel locking screw of FIGS. 1-3 in the process of being inserted into the novel plate of FIG. 1.

FIG. 4 is a partial cross-sectional view of the cervical plate locking mechanism 10 of FIG. 1, the novel locking screw 14 of FIGS. 1-3 in the process of being inserted into the novel plate 12 of FIG. 1. It should be noted that the head portion 19 of the locking screw 14, and specifically the lower, outer portion of each of the plurality of petal structures 20, optionally incorporates a recessed or otherwise weakened area 24, or flexure, in order to facilitate the flexibility and/or outward biasing of the plurality of petal structures 20 by the c-ring 16 or other comparable mechanism, after it is inserted into the inner groove 22 that is manufactured into the middle, inner portion of each of the plurality of petal structures 20. Each of the one or more screw-receiving holes 13 of the plate 12 includes an annular lip structure 26 through which the head portions 19 of the locking screws 14 are inserted (with a compression-expansion action). This annular lip structure 26 serves to retain the head portion 19 of the given locking screw 14 once it is fully inserted and expanded, thereby preventing the reverse threading or backing out of the locking screw 14. Optionally, the inner annular surface 28 of each of the screw-receiving holes 13 of the plate 12 is curved in a generally concave manner, but shaped such that the lead-in torque of a given locking screw 14 is less than the lead-out torque or the locking screw 14, i.e. the inner annular surface angles adjacent to the outer surface 29 of the plate 12 (at the "top" and "bottom" of the lip structure 26) vary as experienced by an inserted locking screw 14 versus a removed locking screw 14, with the "top" angle being greater (more vertical or steep) and the "bottom" angle being smaller (more horizontal or shallow), for example.

Figure 5:
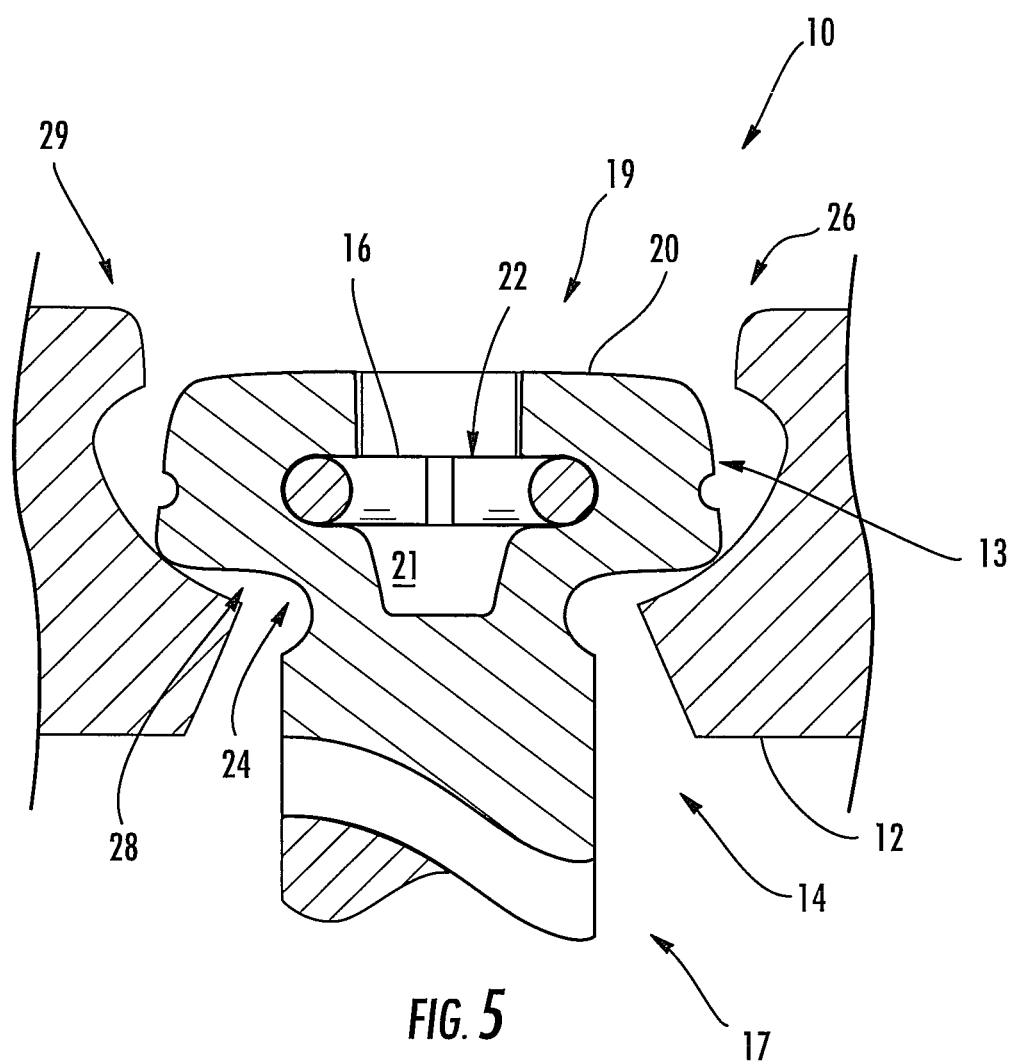
FIG. 5 is a partial cross-sectional view of the cervical plate locking mechanism of FIGS. 1 and 4, the novel locking screw of FIGS. 1-4 being fully inserted into the novel plate of FIGS. 1 and 4.

FIG. 5 is a partial cross-sectional view of the cervical plate locking mechanism 10 of FIGS. 1 and 4, the novel locking screw 14 of FIGS. 1-4 being fully inserted into the novel plate 12 of FIGS. 1 and 4. Again, it should be noted that the head portion 19 of the locking screw 14, and specifically the lower, outer portion of each of the plurality of petal structures 20, optionally incorporates a recessed or otherwise weakened area 24, or flexure, in order to facilitate the flexibility and/or outward biasing of the plurality of petal structures 20 by the c-ring 16 or other comparable mechanism, after it is inserted into the inner groove 22 that is manufactured into the middle, inner portion of each of the plurality of petal structures 20. Each of the one or more screw-receiving holes 13 of the plate 12 includes an annular lip structure 26 through which the head portions 19 of the locking screws 14 are inserted (with a compression-expansion action). This annular lip structure 26 serves to retain the head portion 19 of the given locking screw 14 once it is fully inserted and expanded, as illustrated, thereby preventing the reverse threading or backing out of the locking screw 14. Optionally, the inner annular surface 28 of each of the screw-receiving holes 13 of the plate 12 is curved in a generally concave manner, but shaped such that the lead-in torque of a given locking screw 14 is less than the lead-out torque or the locking screw 14, i.e. the inner annular surface angles adjacent to the outer surface 29 of the plate 12 (at the "top" and "bottom" of the lip structure 26) vary as experienced by an inserted locking screw 14 versus a removed locking screw 14, with the "top" angle being greater (more vertical or steep) and the "bottom" angle being smaller (more horizontal or shallow), for example.

Figure 6:
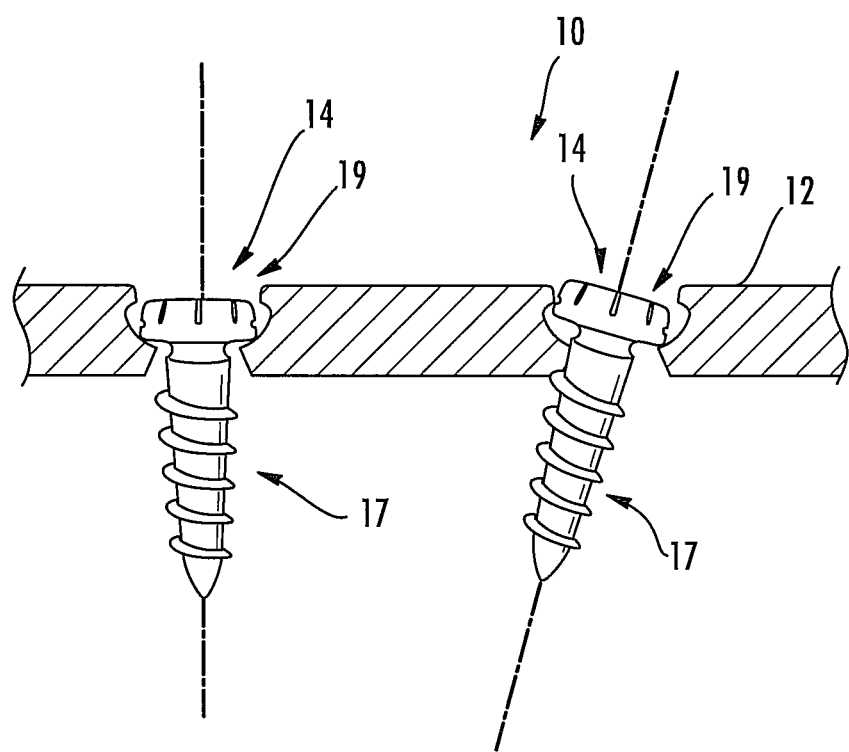
FIG. 6 is a partial cross-sectional view of the cervical plate locking mechanism of FIGS. 1, 4, and 5, the novel locking screws of FIGS. 1-5 being inserted into the novel plate of FIGS. 1, 4, and 5 at various exemplary angles.
Figure 7:
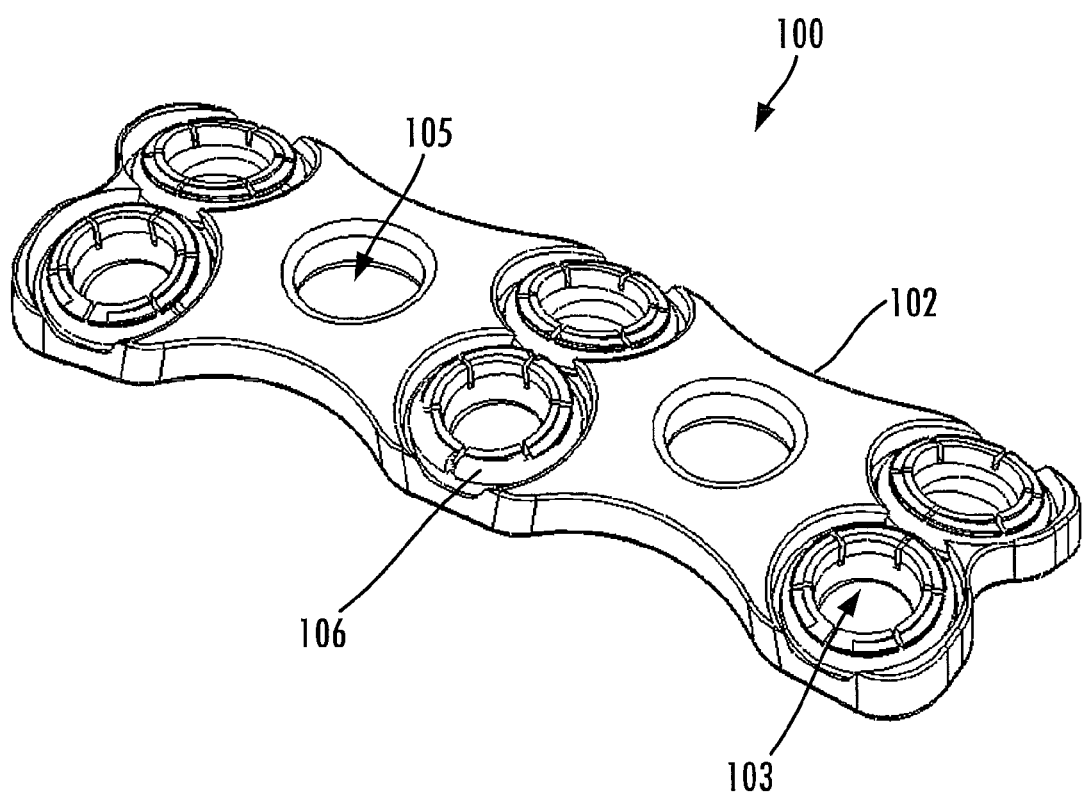
FIG. 7 is a perspective view of another exemplary embodiment of the cervical plate locking mechanism of the present invention, the cervical plate locking mechanism again including both novel locking plate and novel screw (not illustrated) designs.
Figure 8:
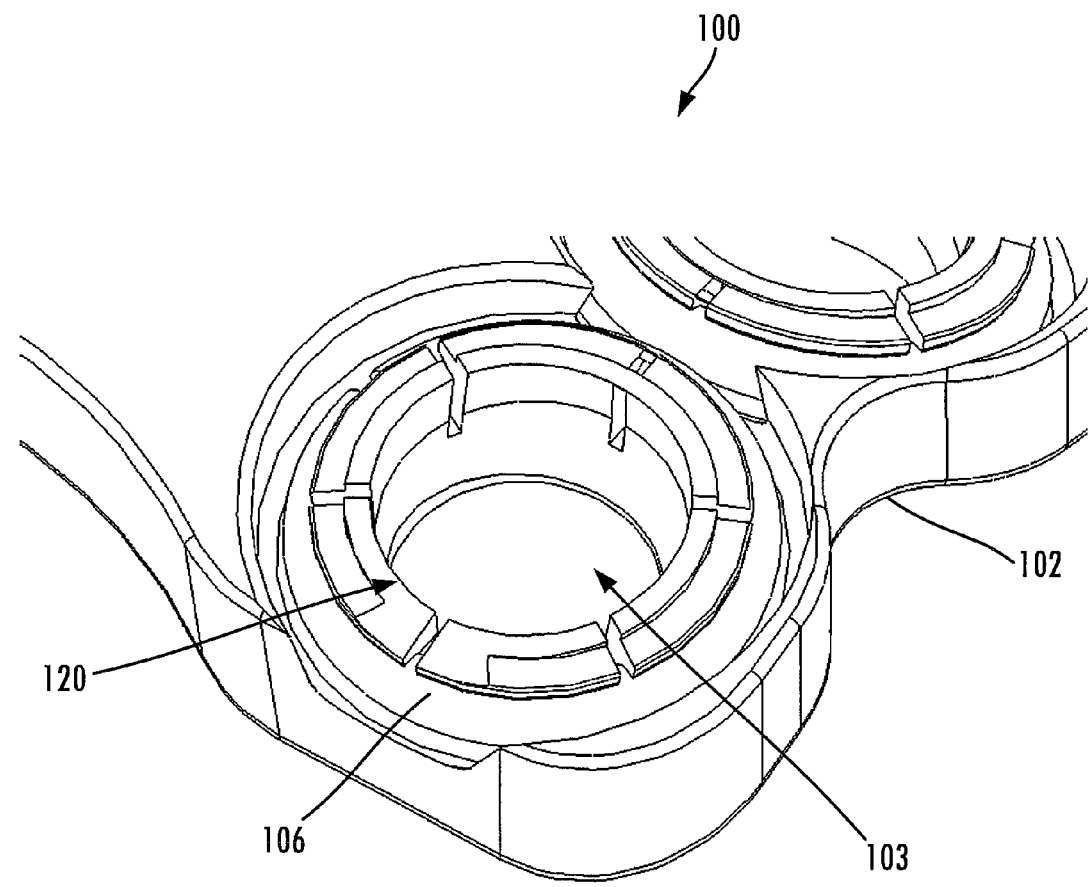
FIG. 8 is a partial perspective view of the cervical plate locking mechanism of FIG. 7, the novel locking plate incorporating one or more screw-receiving holes each including a plurality of petal structures configured to engage and retain the novel screws (not illustrated)
Figure 9:
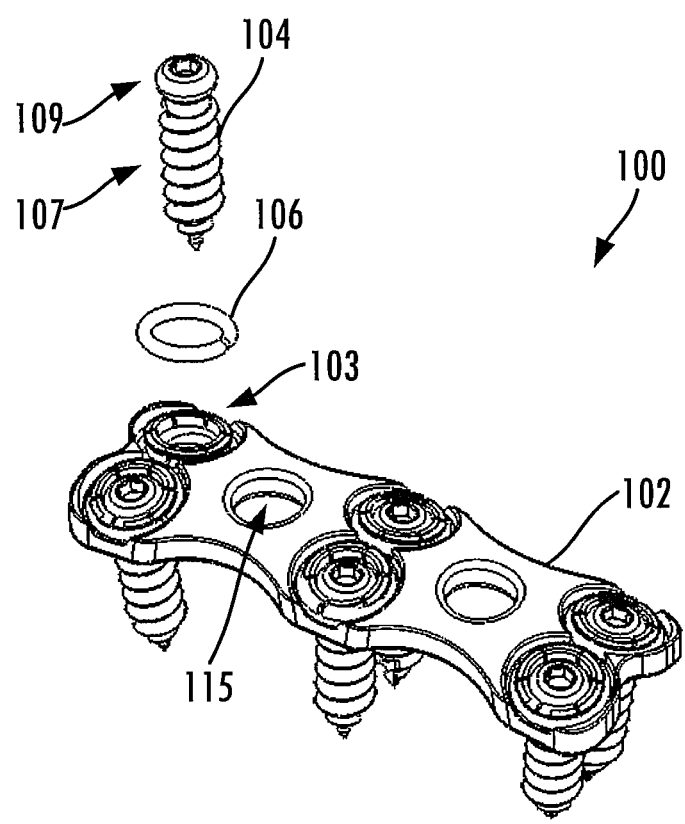
FIG. 9 is an exploded perspective view of the cervical plate locking mechanism of FIGS. 7 and 8, a novel screw being inserted into a screw-receiving hole of the novel locking plate.
Figure 10:
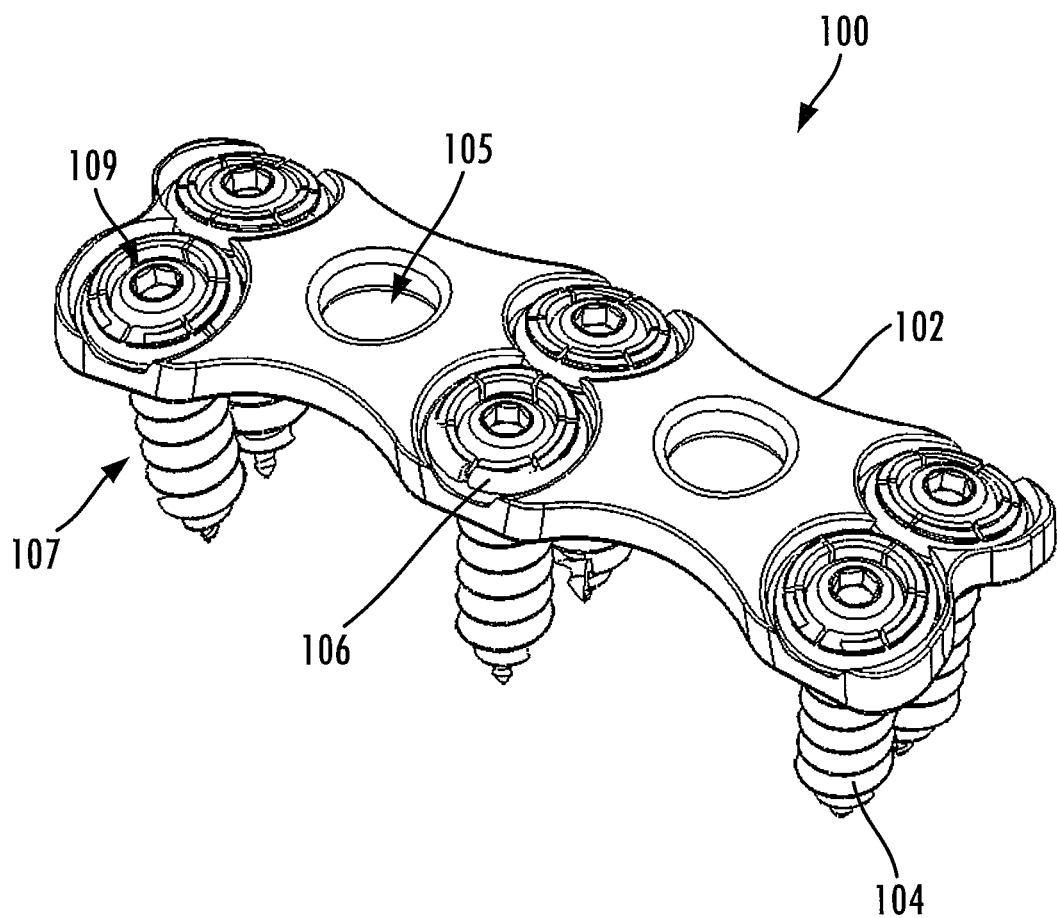
FIG. 10 is a perspective view of the cervical plate locking mechanism of FIGS. 7-9, novel screws fully inserted into all of the screw-receiving holes of the novel locking plate.
Figure 11:
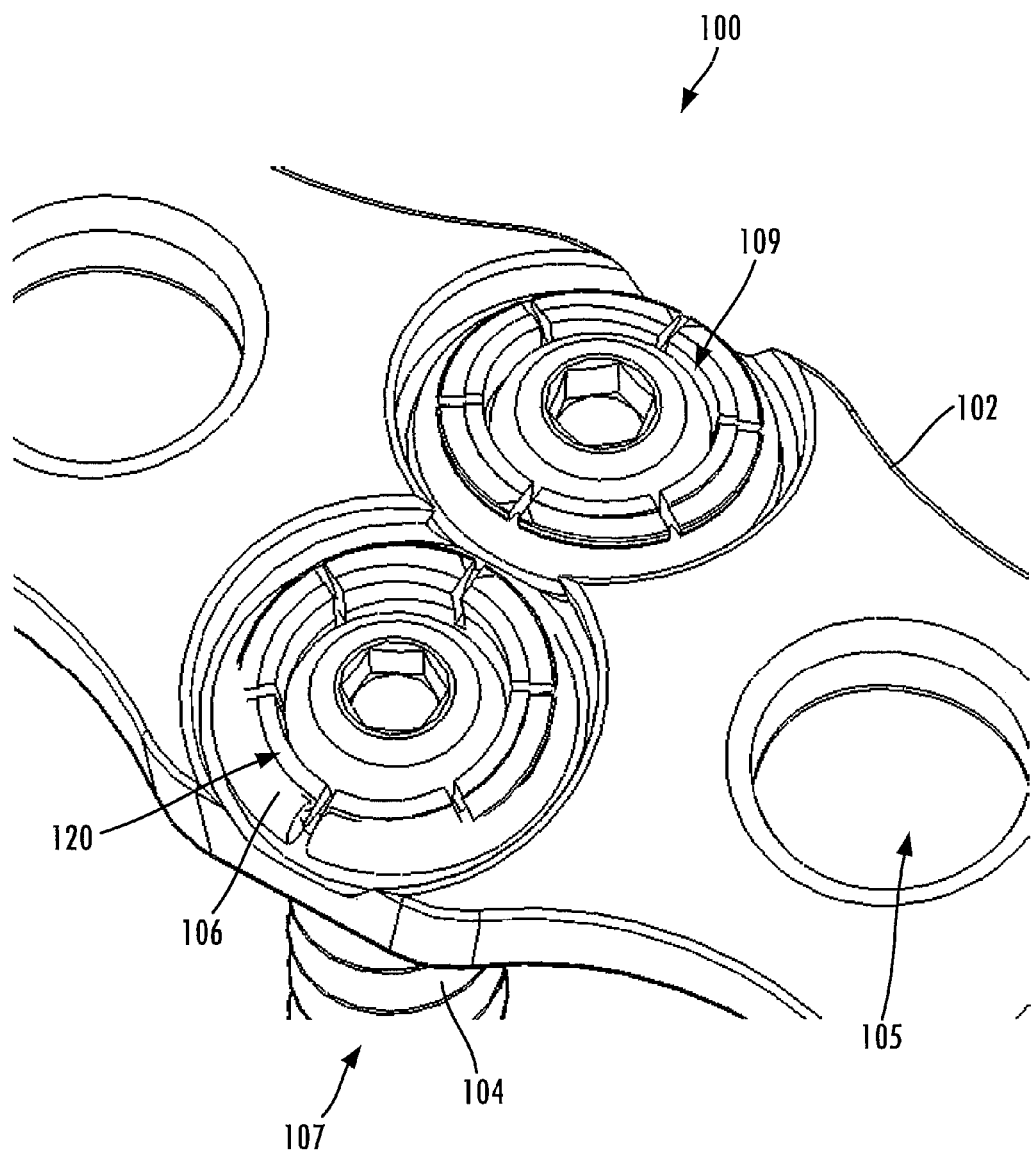
FIG. 11 is a partial perspective view of the cervical plate locking mechanism of FIGS. 7-10, novel screws fully inserted into all of the screw-receiving holes of the novel locking plate.
Figure 12:
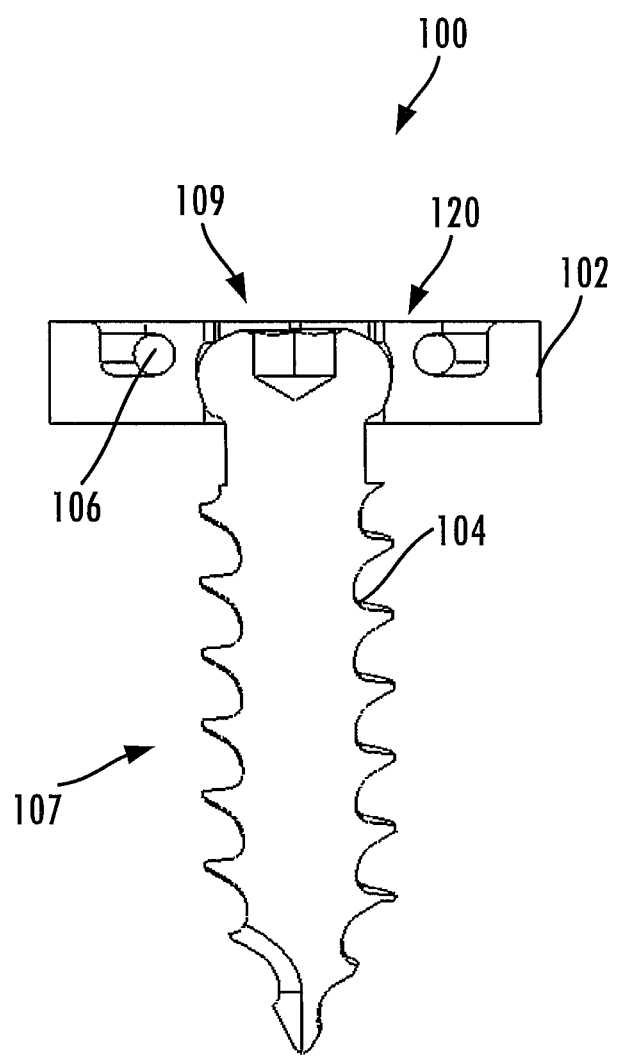
FIG. 12 is a partial cross-sectional view of the cervical plate locking mechanism of FIGS. 7-11, a novel screws fully inserted into a screw-receiving holes of the novel locking plate.

FIG. 6 is a partial cross-sectional view of the cervical plate locking mechanism 10 of FIGS. 1, 4, and 5, the novel locking screws 14 of FIGS. 1-5 being inserted into the novel plate 12 of FIGS. 1, 4, and 5 at various exemplary angles relative to both the plate 12 and the underlying vertebrae. In this embodiment, each of the receiving wells may be asymmetrical in shape such that the head portion 19 of each of the locking screws 14 snugly and securely engages the receiving well, although this is not necessarily illustrated. In other words, each of the receiving wells may be appropriately angled in the plate 12 in order to receive each of the angled locking screws 14.

Referring to FIGS. 7-12, in another exemplary embodiment of the cervical plate locking mechanism 100 of the present invention, the cervical plate locking mechanism 100 again includes both novel locking plate and novel screw designs, as are described in greater detail herein below. Specifically, the cervical plate locking mechanism 100 includes a locking plate 102 that is configured to be securely fixed to adjacent vertebrae of the cervical spine or the like via one or more screws 104 and one or more c-rings 106. The keyed screwdriver (not illustrated) is, used to drive the one or more screws 104 through the locking plate 102 and into the adjacent vertebrae. The locking plate 102 includes one or more screw-receiving holes 103 and, optionally, one or more access holes 105 for the placement of one or more bone grafts, biocompatible inserts, or the like. Preferably, the locking plate 102 is manufactured from a biocompatible material and is sized such that it achieves its intended purpose. Material, shape, and size selection is well known to those of ordinary skill in the art. Each of the one or more screws 104 includes a threaded portion 107 and a head portion 109. The threaded portion 107 of each of the one or more screws 104 is configured to pass through the one or more screw-receiving holes 103 of the locking plate 102 and securely fix the locking plate 102 to the adjacent vertebrae. Thread selection is well known to those of ordinary skill in the art. The head portion 109 of each of the one or more screws 104 is configured to securely engage each of the one or more screws 104 with the locking plate 102. As described in greater detail herein below, a plurality of petal structures 120 disposed about each of the screw-receiving holes 103 are inwardly biased by the c-ring 106. The c-ring 106, or other comparable mechanism, and the plurality of petal structures 120 are expanded and subsequently allowed to contract as the head portion 109 of a screw 104 is disposed in the receiving well of the given screw-receiving hole 103. This insertion is accomplished using a matching flat, triangle, square, star, hexagon, octagon, or other keyed screwdriver, as appropriate. Preferably, the shape of the outside of the head portion 109 of each of the screws 104 substantially corresponds to the shape of the inside of the associated receiving well, although this is not a requirement. Thus, in this exemplary embodiment, the plurality of petal structures 120 and the c-ring 106 have been shifted from the one or more screws 104 to the locking plate 102, accomplishing the same purposes.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A cervical plate system, comprising:
a locking plate defining one or more screw-receiving holes, wherein a perimeter of each of the one or more screw-receiving holes is formed by a plurality of petal structures;
a biasing member configured to be positioned concentrically about the plurality of petal structures, wherein the biasing member is further configured to provide an inward bias of the plurality of petal structures when the biasing member is positioned concentrically about the plurality of petal structures; and
one or more screws, wherein each of the one or more screws comprises a head portion configured to selectively be disposed within and retained by the plurality of petal structures.

2. The cervical plate system of claim 1, wherein the biasing member comprises a c-ring configured to be positioned concentrically about the plurality of petal structures.

3. The cervical plate system of claim 1, wherein the biasing member is configured to be positioned flush with or beneath a surface of the locking plate.

4. The cervical plate system of claim 1, further comprising at least one access hole configured to receive a bone graft or biocompatible insert therethrough.

5. The cervical plate system of claim 1, wherein each of the screw-receiving holes comprises a receiving well.

6. The cervical plate system of claim 5, wherein the head portions of the one or more screws are configured to at least substantially correspond to a shape of the receiving well.

7. The cervical plate system of claim 1, wherein the biasing member is a separate element from the locking plate, and wherein the biasing member is configured to be selectively coupled with the locking plate by inserting the biasing member into one of the screw-receiving holes.

8. The cervical plate system of claim 1, wherein the one or more screw-receiving holes comprise circular holes.

9. The cervical plate system of claim 8, wherein the petal structures extend around an entire perimeter of each of the one or more screw-receiving holes.

10. The cervical plate system of claim 1, wherein the biasing member comprises a circular shape.

11. The cervical plate system of claim 1, wherein the petal structures extend around an entire perimeter of each of the one or more screw-receiving holes.

* * * * *